United States Patent [19]

Spada et al.

[11] Patent Number: 4,829,066

[45] Date of Patent: May 9, 1989

[54] PYRIDOOXAZINONE-PYRIDAZINONE AND PYRAZOLONE COMPOUNDS, CARDIOTONIC COMPOSITIONS INCLUDING THE SAME, AND THEIR USE

[75] Inventors: Alfred P. Spada, Ambler; William L. Studt, Harleysville; Henry F. Campbell, Lansdale; Donald E. Kuhla, Doylestown, all of Pa.

[73] Assignee: Rorer Pharmaceutical Corporation, Fort Washington, Pa.

[21] Appl. No.: 47,395

[22] Filed: May 8, 1987

[51] Int. Cl.$^4$ .................. A61K 31/535; C07D 498/04
[52] U.S. Cl. .................. 514/230.5; 514/211; 514/254; 514/302; 540/490; 540/494; 544/91; 544/105; 544/238; 546/116
[58] Field of Search .............. 514/234, 230.5; 544/91, 544/105

[56] References Cited

U.S. PATENT DOCUMENTS

| | | | |
|---|---|---|---|
| 3,854,926 | 12/1974 | Senkbeil | 544/105 X |
| 3,984,405 | 10/1976 | Krapcho | 544/105 |
| 4,725,686 | 2/1988 | Kuhla et al. | 544/238 |

OTHER PUBLICATIONS

Heilmann et al., Chemical Abstracts, vol. 105 (1986), 226,602w.

*Primary Examiner*—Richard L. Raymond

[57] ABSTRACT

This invention relates to substituted pyridooxazinone pyridazinone and pyrazolone compounds, which are useful as cardiotonic agents for the treatment of congestive heart failure. This invention also relates to methods for increasing cardiac contractility using said compounds, and pharmaceutical compositions including said compound.

8 Claims, No Drawings

PYRIDOOXAZINONE-PYRIDAZINONE AND PYRAZOLONE COMPOUNDS, CARDIOTONIC COMPOSITIONS INCLUDING THE SAME, AND THEIR USE

FIELD OF INVENTION

This invention relates to substituted pyridooxazinone pyridazinone and pyrazolone compounds, which are useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Inotropic drugs include the 5-pyridyl substituted pyridones disclosed in U.S. Pat. Nos. 4,004,012; 4,072,746; 4,137,233; 4,199,586; 4,271,168; and 4,107,315; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572 and the 5-phenylthiazole compounds disclosed in U.S. Pat. No. 4,418,070.

Cardiotonic bicyclic heteroaryl-5-substituted pyridyl compounds are disclosed in U.S. PCT/US83/01285, and cardiotonic dizaheterocyclic-5-substituted pyridyl compounds are disclosed in U.S. Pat. No. 4,432,979 and U.S. Pat. Nos. 4,514,400 and 4,539,321, all of which are assigned to the same assignee as the present application.

Cardiotonic 4,5-dihydro-5-[4-(H-imidazol-1-yl)phenyl]3(2)-pyridazinones are disclosed in Bristol et al., J. Med. Chem. 22, 1099 (1984); cardiotonic imidazolyl substituted pyridazinones are disclosed in U.S. Pat. No. 4,521,416, and cardiotonic benzothiazolone substituted pyridazinones are disclosed in published EPO Patent Application Ser. No. 84108656.4 (Publ. No. 0132817). Cardiotonic compounds including a pyrazole group are disclosed in published EPO patent application Ser. No. 84303456.2 (Publ. No. 0126651) and U.S. Pat. No. 4,526,895 and 4,526,982.

SUMMARY OF THE INVENTION

The present invention relates to a method for increasing cardiac contractility in humans and other mammals comprising the administration of an effective inotropic amount of a pyridooxazinone pyridazinone or pyrazolone.

This invention comprises particularly the administration to a patient of an effective inotropic amount of a pyridooxazinone compound within the scope of Formula I:

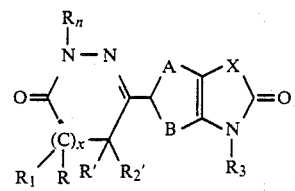

where
A is —C= or —N=;
B is —C=C—; —C=N— or —N=C; provided A+B together contain one nitrogen atom;
x is 0 or 1;
X is —(CR$_4$R$_5$)$_a$—O—(CR$_4$R$_5$)$_b$—
where a and b are 0, 1 or 2 and a+b=0, 1 or 2;
R, R$_1$, R$_3$, R$_4$ and R$_5$ are each independently
  hydrogen,
  alkyl or
  aralkyl;
R$_4$ may also be aryl;
R$_n$ is hydrogen,
  alkyl,
  aralkyl,
  acyl,
  carbalkoxy,
  carbamyl,
  carbalkoxyalkyl,
  hydroxyalkyl,
  alkoxyalkyl or
  amidino;
R groups on vicinal carbon atoms may together form a carbon-carbon double bond when R$_n$ is hydrogen and x=1;
R$_4$ and R$_5$ geminal groups may together form a spiro substituent, —(CH$_2$)$_d$—, where d is 2 to 5;
R$_2$ is hydrogen or —(CH$_2$)$_y$—Y where y is 1-3 and Y is hydrogen,

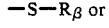

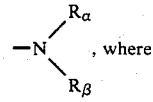

where R$_\alpha$ is hydrogen,
  alkyl or
  acyl and;
R$_\beta$ is hydrogen or
  alkyl; and
R$_\alpha$ and R$_\beta$ together may form a 3-7 membered ring which may also contain 0-2 additional hetero atoms selected from N, O and S; or a pharmaceutically acceptable salt thereof.

DETAILED DESCRIPTION

The compounds of this invention which have particular usefulness as cardiotonic agents are described by Formula I wherein the pyridooxazinone ring is described by one of Formulae IIa–IIc, IIIa–IIIc or IVa–IVc:

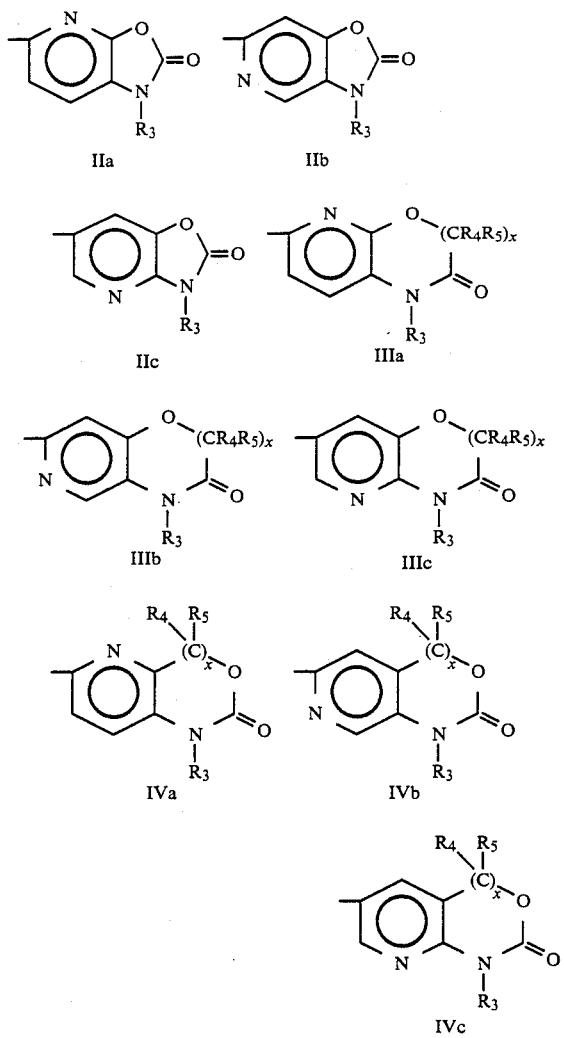

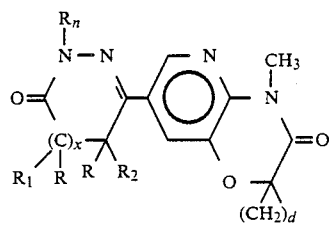

wherein:

R₃, R₄, and R₅ are as described above.

A more preferred class of compounds within the present invention includes compounds of Formula I wherein R₂ is —(CH₂)$_y$—Y, the more preferred compounds being those where Y is

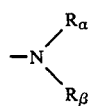

The mono- and di-alkylamino substitution or formation of a hetero ring are specially preferred.

Most preferred compounds are those disclosed by Formula IIIc where X is 1.

A special embodiment of the present invention comprises compounds of Formula I where R₃ and R₄ are hydrogen or lower alkyl.

Another special embodiment of the present invention comprises compounds of Formula I where R₄ and R₅ form a spiro ring system, an example of which is shown by Formula V:

Other preferred embodiments include those compounds according to Formula I wherein:

x is 1 and vicinal R groups form a double bond.

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

"Aralkyl" means an alkyl group substituted by an aryl radical. The preferred aralkyl groups are benzyl or phenethyl.

"Alkoxy" means an alkyl oxy group in which "alkyl" is as previously described. Lower alkoxy groups are preferred and include methoxy, ethoxy, n-propoxy, i-propoxy, sec-propoxy, n-butoxy among others.

"Hydroxyalkyl" means an alkyl group substituted by a hydroxy group. Hydroxy lower alkyl groups are preferred and include hydroxymethyl, 2-hydroxyethyl, 2-hydroxypropyl, and 3-hydroxypropyl.

"Acyl" means an organic radical derived from an organic acid by the removal of its hydroxyl group. Preferred acyl groups are acetyl, propionyl, benzoyl, etc.

Certain of the compounds encompassed within the present invention may exist in enolic or tautomeric forms, and all of these forms are considered to be included within the scope of this invention.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds within the scope of Formula I may be prepared in accordance with the following reaction sequences.

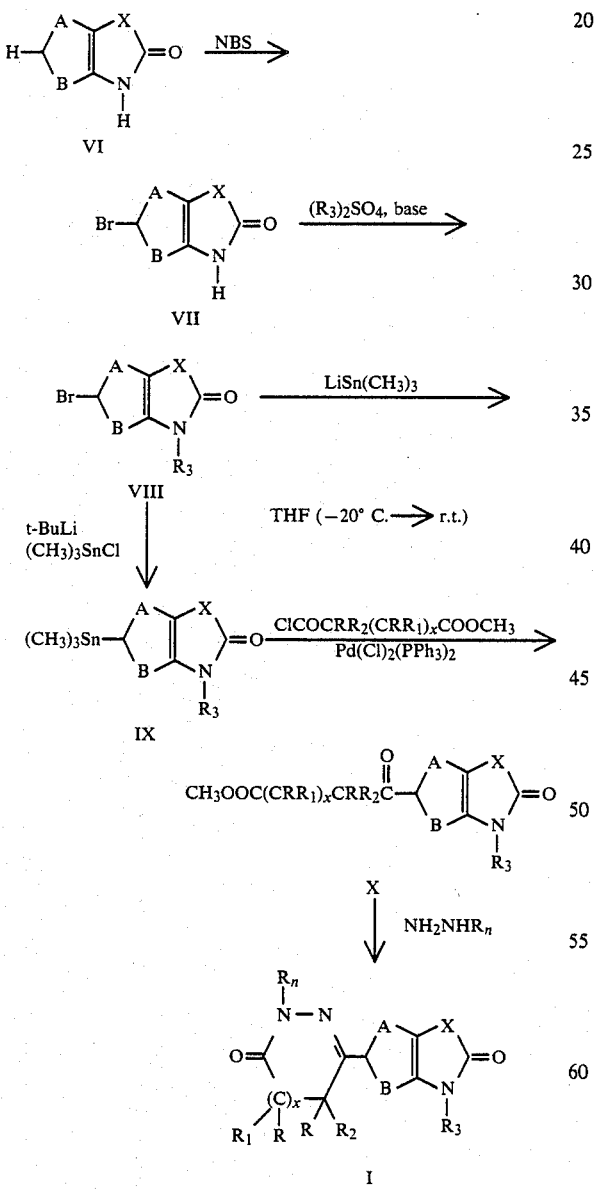

Bromination of a pyridooxazinone compound of Formula VI results in the corresponding brominated product (VII). This can be carried out by brominating techniques such as with N-bromosucciminide. Bromination occurs in the pyrido ring, para to the nitrogen of the oxazinone. Alkylation or aralkylation of the oxazinone nitrogen (VIII) followed by treatment with lithium trimethylstannane gives the trimethylstannane intermediate IX. The latter is carried out in an aprotic solvent at about −20° C. to about room temperature. The stannane may also be formed from the bromide VIII by treatment with t-butyl lithium and trimethyltin chloride. When the stannane is treated with a palladium catalyst such as $Pd(Cl)_2$ $(PPh_3)_2$ in a solvent such as toluene or THF in the presence of carbomethoxy propionyl chloride, then the corresponding 3-(methoxycarbonyl)-propionyl compound is prepared (X). This is then ring closed to the pyridazinone with hydrazine to obtain compounds of Formula I.

When the keto acid compound of Formula X is treated with an amine of the Formula $$HN\begin{matrix}R_\alpha\\R_\beta\end{matrix}$$

and formaldehyde, the corresponding Mannich base XI results. This may then be reacted with a hydrazine to obtain the R-substituted product.

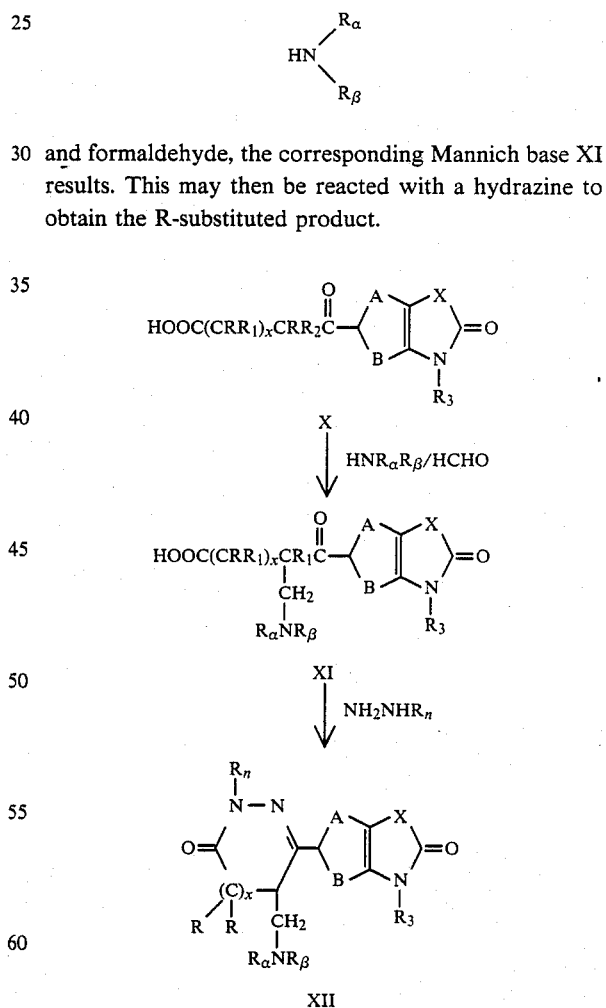

When Y is —O—$R_\alpha$ the enolate anion of X is treated with ethylformate to generate XIII which upon reduction and ring closure with a hydrazine gives the desired product.

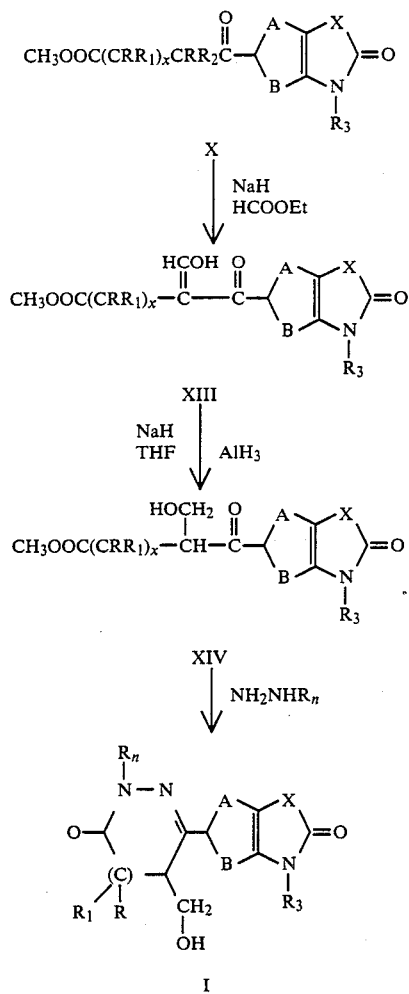

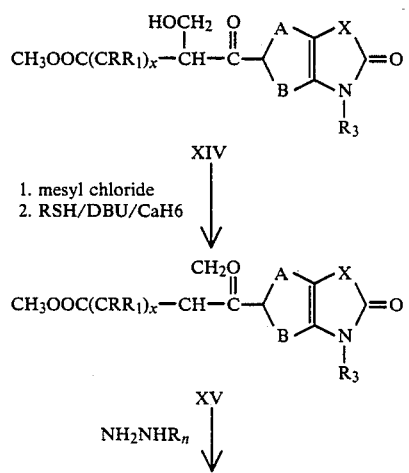

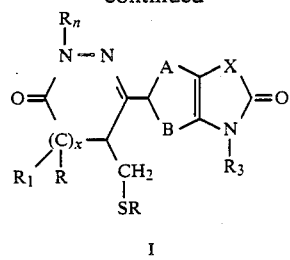

The starting materials of this invention are either known or can be prepared by the following reaction sequences.

When 2-amino-3-hydroxypyridine is treated with sodium hydride followed by ring closure with a haloacetate or acid halide of the formula:

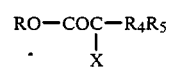

The pyridooxazinones are formed.

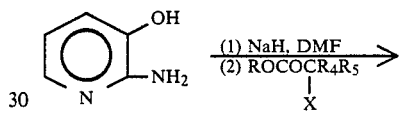

When the seven membered ring is desired, the reaction is carried out using the halopropionate.

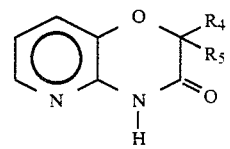

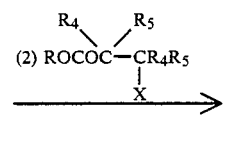

The five membered ring is prepared by reacting 2-amino-3-hydroxypyridine either with phosgene or N,N-carbonyldiimidazole.

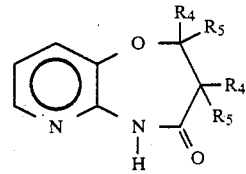

Those compounds where the oxygen atoms of the pyridooxazinone ring is not directly on the pyridine ring can be prepared from the 2-aminonicotinic acid or ester, reducing the latter to the corresponding alcohol and ring closing as in the above synthesis.

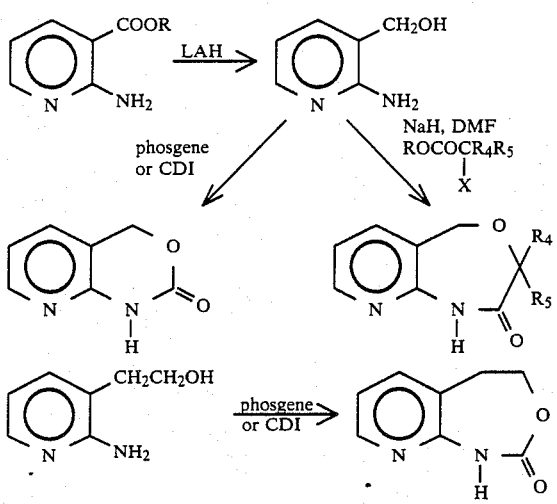

When the starting pyridine is 3-amino-4-hydroxypyridine or 2-hydroxy-3-aminopyridine then the corresponding pyridooxazinone is prepared.

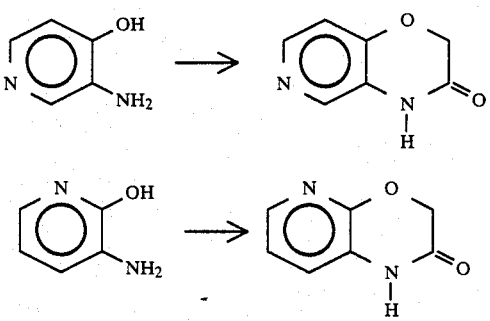

When R$_3$ substitute is desired then the corresponding R$_3$ substituted aminopyridine would be used.

The compounds of Formula 1 possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The ganglionic-beta blocked anesthetized dog procedure is one such standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncanulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37° C.

Following a 30 min postsurgical stabilization period, control values are recorded. Myocardial depression is induced by ganglionic and beta receptor blockade. Initially, the responsiveness of the autonomic nervous system is assessed by performing a 30 sec bilateral carotid occlusion (BCO). Ten minutes later, a saline solution of isoproterenol 0.3 mg/kg, i.v. is administered to assess beta receptor integrity. Ten minutes after that, a saline solution of mecamylamine 2 mg/kg, i.v. is infused, followed by a saline solution of propranolol 1 mg/kg, i.v. plus 0.3 mg/kg/hr. Twenty minutes later, a second BCO is performed to demonstrate ganglionic blockade followed by a second injection of saline isoproterenol 0.3 mg/kg, i.v. to demonstrate beta blockade. Ten minutes later, the test compound or vehicle is administered intravenously in ascending doses at 30 min intervals at 1.5 ml/min in a total volume of 3.5 ml. On completion of the experiment, both BCO and isoproterenol challenges are repeated to verify ganglionic and beta blockade.

The results of the blocked dog test show that compounds of the present invention increase contractile force and heart rate, and aortic blood flow in a dose related manner while maintaining arterial pressure.

Additional test procedures which have been found to be an efficient means for ascertaining the inotropic activity of the compounds of this invention are described below.

Guinea Pig Atria Inotropic Screening Concentrations

Guinea pigs are stunned by a sudden blow to the head; their chests are opened and hearts excised and placed in Kreb's medium (concentrations, mM: NaCl, 118.39; KCl, 4.70; MgSO$_4$, 1.18; KH$_2$PO$_4$, 1.18; NaHCO$_3$, 25.00; glucose, 11.66 and CaCl$_2$, 1.25 gassed with a mixture of 95% O$_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 2-gauge silver wire wound into a tight coil approximately 12–14 mm in diameter. Electrodes are connected to a Grass stimulator via Grass constant current unit. Tissues are driven at 90 pulses per minute with 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions calculated via the method of Finney (1971) are compared using Student's t-test.

The following in vitro method is another means for measuring the inotropic potency of the present compounds. This method is a modification of the enzyme inhibition method reported by Thompson and Appleman (1970) and Thompson et al. (1974), and is believed to correlate to in vivo inotropic activity in humans.

Inhibition of Peak III cAMP Phosphodiesterase Activity

The test compounds are included in media comprising a radioactivity labeled substrate ($^3$H-cyclic nucleotide) such as adenosine 3':5'-monophosphate (cyclic AMP) and quanine-3':5'-nucleotidease isolated from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ion exchange resin so that it is not quantitated with the liquid scintillation counter.

Anesthetized Dog Procedure

Male mongrel dogs are anesthetized with pentobarbital (35 mg/kg, i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg, i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with haparinized 50% dextrose solution, and the chest is closed and evacuated.

The dogs are treated daily post-operatively with 600,000 units of penicillin-procaine i.m. for ten days and with chloramphenicol, 500 mg/kg, i.m., every other day for 10 days and allowed at least 7 days recovery before use.

Each dog is trained and acclimated to its environment and the presence of personnel during the experiment. The dogs are fasted overnight before either intravenous or oral administration of the compound. On a test day, the dog is placed in a sling and connected to a recorder (Gould Instruments or Grass Instruments) for measurement of left ventricular pressure, left ventricular dP/dt$_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl; sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The acqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic resonse until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such a patient should be effective to achieve and maintain the desired therapeutic response.

Compounds of this invention may be prepared by the following examples.

EXAMPLE 1

7-[4',5'-DIHYDRO-3'-OXO-(2H)PYRIDAZIN-6'YL]-4-METHYL-2H-PYRIDO[3,2-b]-1,4-OXAZIN-3(4H)-ONE

Step 1. 7-bromo-2H-pyrido[3,2-b]-1,4-oxazin-3(4H)-one

To a solution of 5.6 g 2H-pyrido[3,2-b]-1,4-oxazin-3(4H)-one dissolved in 85 ml of DMF under nitrogen is added 7.96 g NBS in 50 ml of DMF. This is allowed to stir at room temperature overnight. To this is added 35 ml of water and chilled. The solid material which separates is filtered and washed with $3 \times 100$ ml $H_2O$. This is then dried in a vac oven at 70° C. and then used directly in the next step.

Step 2.
7-trimethylstannyl-2H-pyrido[3,2-b]-1,4-oxazin-3(4H)-one

A suspension of 0.24 g of 7-bromo-2H-pyrido[3,2-b]-1,4-oxazin-3(4H)-one in 14 ml THF is added dropwise to a suspension of 0.048 g sodium hydride (previously cleaned with hexanes) at room temperature. After several hours when the addition is complete about 1 ml of HMPA is added. Separately a mixture is prepared consisting of 1.5 ml of methyl lithium (1.4M) added to a solution of hexamethyltin in 5 ml THF. This is chilled to about −20° C. To this latter mixture is added the oxazinone mixture from above and allowed to stir allowing the temperature to rise to room temperature. Stirring is continued for a total of 72 hours. The reaction mixture is then quenched with ammonium chloride and extracted with chloroform. The combined organic layers are washed with brine, dried over sodium sulfate and evaporated to obtain a yellow solid. This material is then dissolved in chloroform and chromatographed; hexanes: ethylacetate (75:25). The material recovered is used directly in the next step.

Step 3.
4-methyl-7-trimethylstannyl-2H-pyrido[3,2-b]-1,4-oxazin-3(4H)-one

To a suspension of 680 mg of 7-trimethylstannyl-2H-pyrido[3,2-b]-1,4-oxazin-3(4H)-one (0.0022 mole) in 10 ml of THF is added 2.4 ml of LiN(TMS)2 (0.0024 mole) in THF. The homogenous solution is maintained under nitrogen at room temperature for 20 min., 300 mg (0.0024 mole) of dimethylsulfate is added and the reaction mixture allowed to stir overnight. The reaction mixture is then quenched with 10 ml of sat. ammonium chloride and extracted with $3 \times 50$ ml ethyl acetate. The ethyl acetate is then washed with $3 \times 10$ ml sat. ammonium chloride, dried over sodium sulfate and concentrated to obtain off white product which is used directly in the next step.

Step 4.
4-methyl-7-(3'-methoxycarbonyl)propionyl-2H-pyrido[3,2-b]-1,4-oxazin-3(4H)-one To an inert system previously dried is added 650 mg (0.002 mole) of 4-methyl-7-trimethylstannyl-2H-pyrido[3,2-b]-1,4-oxazin-3(4H)-one in 4 ml THF, 13 mg of $PdCl_2$ $(PPh_3)_2$ and 36 mg of carbomethoxypropionyl chloride. This is refluxed for 22 hours; diluted with ethylacetate and quenched with 40 ml sat. ammonium chloride. The aqueous layer is extracted with ethyl acetate and the combined organic layer washed with brine and dried over sodium sulfate. A yellow solid results on evaporation to dryness which is chromatographed using ethyl acetate:hexanes (55:45) to give the indicated product which is used directly in the next step.

Step 5.
7-[4',5'-3'-oxo-(2H)pyridazin-6'-yl]4-methyl-2H-pyrido[3,2-b]-1,4-oxazin-3(4H)-one Hydrazine monohydrate (35 mg) is added to a solution of 4-methyl-7-(3'-methoxycarbonyl)propionyl-2H-pyrido[3,2-b]1,4-oxazin-3(4H)-one (160 mg) in 5 ml of ethanol. The reaction mixture is heated to reflux for 3 days. This is then cooled to room temperature, filtered, and upon standing the product separates.

EXAMPLE 2

When carbomethoxy propionyl chloride is replaced in Example 1, Step 4 with carbomethoxy-acetylchloride then the product prepared is 7-[3',4'-dihydro-3'-oxopyrazolin-5'-yl]-4-methyl-2H-pyrido[3,2-b]-1,4-oxazin-3(4H)-one.

EXAMPLE 3

When 2H-pyrido [3,2-b]-1,4-oxazin-3-(4H)-one of Exmple 1, Step 1 is replaced with the compounds of Table I below, then the corresponding product is obtained.

Table I 2H-pyrido[3,2-b]-1,4-oxazin-3(4H)-one
2H-pyrido[4,3-b]-1,4-oxazin-3(4H)-one
2H-pyrido[2,3-b]-1,4-oxazin-3(4H)-one
4H-pyrido[2,3-d][1,3]oxazin-2(1H)-one
4H-pyrido[3,4-d][1,3]oxazin-2(1H)-one
4H-pyrido[3,2-d][1,3]oxazin-2(1H)-one
oxazolo[4,5-b]pyridin-2(3H)-one oxazolo[4,5-c]pyridin-2(3H)-one
oxazolo[5,4-b]pyridin-2(3H)-one
2,3-dihydropyrido[3,2-b][1,4]oxazepin-4(5H)-one
2,3-dihydropyrido[4,3-b][1,4]oxazepin-4(5H)-one
2,3-dihydropyrido[2,3-b][1,4]oxazepin-4(5H)-one
3,5-dihydropyrido[2,3-e]-1,4-oxazepin-2-(1H)-one
3,5-dihydropyrido[3,4-e]-1,4-oxazepin-2-(1H)-one
3,5-dihydropyrido[3,2-e]-1,4-oxazepin-2-(1H)-one
4,5-dihydropyrido[2,3-d]-1,3-oxazepin-2(lH)one
4,5-dihydropyrido[3,4-d]-1,3-oxazepin-2(1H)one
4,5-dihydropyrido[3,2-d]-1,3-oxazepin-2(1H)one

EXAMPLE 4

When dimethylsulfate is replaced in Example 1, Step 3 with benzylbromide, then the corresponding 4-benzyl-7-bromo-2H- pyrido[3,2-b]-1,4-oxazin-3(4H)-one is prepared.

EXAMPLE 5

7-(3'-METHOXYCARBONYL-2'-N-MORPHOLINOMETHYL)PROPIONYL-2H-PYRIDO[3,2-b]-1,4-OXAZIN-3(4H)-ONE

Step 1. A mixture of 4-methyl-7-(3'-methoxycarbonyl)propionyl-2H-pyrido[3,2-b]-1,4-oxazin-3(4H)-one from Example 1, Step 4 (1.59 g, 5.73 mm mol.), morpholine (0.5 g) and 37% aqueous formaldehyde (0.46 g) in 3 ml of $H_2O$ is warmed at 70° C. for 3.5 hours and then at room temperature for 7 days. The aqueous mixture is extracted with chloroform and reduced in volume to generate a suspension which is filtered to give the desired product which is used directly in the next step.

Step 2.
7-[4',5'-dihydro-5'-(n-morpholinomethyl)-3'-oxo-2H-pyridazin-6'-yl]-4-methyl-2H-pyrido[3,2-b]-1,4-oxazin-3(4H)-one A solution of hydrazine monohydrate (0.17 g) and 1.14 g of 4-methyl-7-(3'-methoxycarbonyl)propionyl-2H-pyrido[3,2-b]- 1,4-oxazin-3(4H)-one in 15 ml ethanol is heated to reflux for 1 day. Upon cooling the solid which precipitates is filtered to give the desired product.

EXAMPLE 6

When the product desired has the ring system of the various starting materials of Example 3, then the corresponding product is prepared by following the various steps of Example 1.

EXAMPLE 7

Following the procedure of Example 5 the amines of Table II below may be used in place of morpholine to obtain the corresponding product.

TABLE II
---
ammonia
ethylamine
diethylamine
methylethylamine
cycolhexylamine
ethyleneimine
trimethyleneimine
piperidine
piperazine
N—methylpiperazine
N—phenylpiperazine
N—benzylpiperazine
N—methylimidazolidine
thiomorpholine TABLE II-continued
---
acetamide

EXAMPLE 8

When hydrazine of the foregoing examples is replaced by the substituted hydrazine of Table III below then the corresponding product is obtained.

TABLE III
---
| | |
|---|---|
| $NH_2NHCH_3$ | $NH_2NHCONH_2$ |
| $NH_2NHCH_2CH_3$ | $NH_2NHC(=NH)NH_2$ |
| $NH_2NHCH_2Ph$ | $NH_2NHCONHSO_2$—p-toly |
| $NH_2NH(CH_2)_2Ph$ | $NH_2NHSO_2$—p-tolyl |
| $NH_2NHCOCH_3$ | |
| $NH_2NHCH_2CH_2OH$ | |
| $NH_2NHCH_2CO_2CH_2CH_3$ | |

EXAMPLE 9

Following the procedures of the foregoing examples the following representative compounds may be prepared.

7-[4'5'dihydro-3'-oxo-2(H)pyridazin-6'yl]-4-methyl-2H-pyrido[4,3-b]-1,4-oxazin-3(4H)-one
7-[4'5'-dihydro-3'-oxo-2(H)pyridazin-6'yl]-4-methyl-2H-pyrido[2,3-b]-1,4-oxazin-3(4H)-one
6-[4'5'-dihydro-3'Z-oxo-2(H)pyridazin-6'yl]-3-methyloxazolo[4,5-b]pyridin-2(3H)-one
6-[4'5'-dihydro-3'-oxo-2(H)pyridazin-6'yl]-3-methyloxazolo[4,5-c]pyridin-2(3H)-one
6-[4'5'-dihydro-3'-oxo-2(H)pyridazin-6'yl]-3-methyloxazolo[5,4-c]pyridin-2(3H)-one
6-[4'5'-dihydro-3'-oxo-2(H)pyridazin-6'yl]-1-methyl-4H-pyrido[2,3-d][1,3]oxazin-2(1H)-one
8-[4'5'-dihydro-3'-oxo-2(H)pyridazin-6'yl]-5-methyl-2,3-dihydropyrido[3,2-b][1,4]oxazepin-4(5H)-one
8-[4'5'-dihydro-3'-oxo-2(H)pyridazin-6'yl]-5-methyl-2,3-dihydropyrido[4,3-b][1,4]oxazepin-4(5H)-one
5'-dihydro-3'-oxo-2(H)pyridazin-6'yl]-1-methyl-2,3-dihydropyrido[4,3-b][1,4]oxazepin-4-(5H)-one
7-[4'5'-dihydro-3'-oxo-2(H)pyridazin-6'yl]-1-methyl-3,5-dihydropyrido[2,3-c]-1,4-oxazepin-2(1H)-one
7-[5'-aminomethyl-4',5'-dihydro-3'-oxo-2(H)pyridazin-6'-yl]-4-methyl-2H-pyrido[3,2-b]-1,4-oxazin-3(4H)-one
7-[5',5'-dimethylaminomethyl-4',5'-dihydro-3'-oxo-2(H)-pyridazin-6'-yl]-4-methyl-2H-pyrido[3,2-b]-1,4-oxazin(3(4H)-one
7-[5'-(N-methylpiperazinylmethyl)-4',5'-dihydro-3'-oxo-2(H)pyridazin-6'-yl]-4-methyl-2H-pyrido[3,2-b]-1,4-oxazin-3(4H)-one
7-[5'-(N-methylpiperdinylmethyl)-4',5'-dihydro-3'-oxo-2(H)pyridazin-6'-yl]-4-methyl-2H-pyrido[3,2-b]-1,4-oxazin-3(4H)-one
7-[5'-methoxymethyl-4',5'-dihydro-3'-oxo-2(H)-pyridazin-6'-yl]-4-methyl-2H-pyrido[3,2-b]-1,4-oxazin-3(4H)-one
7-[5'-thiomethyl-4',5'-dihydro-3'-oxo-2(H)-pyridazin-6'-yl]-4-methyl-2H-pyrido[3,2-b]-1,4-oxazin-3(4H)-one
7-[5'-methyl-4',5'-dihydro-3'-oxo-2(H)-pyridazin-6'-yl]-4-methyl-2H-pyrido[3,2-b]-1,4-oxazin-3(4H)-one
7-[2',5'-dimethyl-4',5'-dihydro-3'-oxo-2(H)-pyridazin-6'-yl]-4-methyl-2H-pyrido[3,2-b]-1,4-oxazin-3(4H)-one
7-[4',5'-dihydro-3'-oxo-2(H)pyridazin-6'-yl]-4-ethyl-2H-pyrido[3,2-b]-1,4-oxazin-3(4H)-one 7-[4',5'-dihydro-3'-oxo-2(H)pyridazin-6'-yl]-
   2Hpyrido[3,2-b]-1,4-oxazin-3(4H)-one
7-[4',5'-dihydro-3'-oxo-2(H)pyridazin-6'-yl]-2,2,4-
   trimethyl-2H-pyrido[3,2-b]-1,4-oxazin-3(4H)-one
7-[4',5'-dihydro-3'-oxo-2(H)pyridazin-6'-yl]-2-methyl-
   2H-pyrido[3,2-b]-1,4-oxazin-3(4H)-one
7-[4',5'-dihydro-3'-oxo-2(H)pyridazin-6'-yl]-2,4-dimeth-
   yl-2H-pyrido[3,2-b]-1,4-oxazin-3(4H)-one
7-[4',5'-dihydro-3'-oxo-2(H)pyridazin-6'-yl]-2-phenyl-
   2H-pyrido[3,2-b]-1,4-oxazin-3(4H)-one

We claim:

1. A compound which is 7-[4',5'-dihydro-2',5'-dimethyl-3'-oxo-(2H)pyridazin-6'-yl]-4-methyl-2H-pyrido-[3,2]-1,4-oxazine-3(4)-one or a pharmaceutically acceptable salt thereof.

2. A compound, which is 7-[4,,5,-dihydro-2,5,-dimethyl-3'-oxo-(2H)pyridazin-6'-yl]-4-methyl-2H-pyrido[3,2-b]-1,4-oxazin-3(4H)-one or a pharmaceutically acceptable salt thereof.

3. A compound which is 7-[4',5'-dihydro-5'-(N,N-dimethylaminomethyl)-3'-oxo-(2H)-pyridazin-6']-4-methyl-2H-pyrido[3,2-b]-1,4-oxazin-3(4H)-one or a pharmaceutically acceptable salt thereof.

4. A compound which is 7-[4',5'-dihydro-5'-(N-morpholinomethyl)-3,-oxo-(2H) pyridazin-6,-yl]-4-methyl-2H-pyrido[3,2-b]-1,4-oxazin-3(4H)-one or a pharmaceutically acceptable salt thereof.

5. A compound which is 7-[4',5'-dihydro-5'-(N-morpholinomethyl)-2'-methyl-3'-oxo-(2H)-pyridazin-6,-yl]-4-methyl-(2H)-pyrido[3,2-b]-1,4-oxazin-3(4)-one or a pharmaceutically acceptable salt thereof.

6. A compound which is 7-[3'-oxo-(2H)pyridazin-6'-yl]-2H-pyrido[3,2-b]-1,4-oxazin-3(4H)-one or a pharmaceutically acceptable salt thereof.

7. A method for increasing cardiotonic contractility in a patient requiring such treatment which comprises administering to such patient an effective positive inotropic amount of a compound selected from the group consisting of 7-[4',5'-dihydro-3,-oxo-(2H) pyridazin-6'-yl]-4-methyl-2H-pyrido-[3,2-b]-1,4-oxazin-3(4H)-one, 7-[4',5'-dihydro-2',5'-dimethyl-3,-oxo-(2H) pyridazin-6,-yl]-4-methyl-2H-pyrido[3,2-b]-1,4-oxazin-3 (4H)-one, 7-[4',5'-dihydro-5'-(N,N-dimethylaminomethyl)-3,-oxo-(2H) -pyridazin-6,-yl]-4-methyl-2H-pyrido[3,2-b]-I,4-oxazin-3 (4H)-one, 7-[4',5'-dihydro-5'-(N-morpholinomethyl)-3,-oxo-(2H) pyridazin-6,-yl]-4methyl-2H-pyrido[3,2-b]-1,4-oxazin-3 (4H)-one, 7-[4',5'dihydro-5'-(N-morpholinomethyl)-2,-methyl-3'-oxo-(2H)-pyridazin-6,-yl]-4-methyl-(2H)-pyrido[3,2-b]-I,4-oxazin-3(4H)-one and 7-[3,-oxo-(2H)pyridazin-6,-yl]-2H-pyrido [3,2-b]-1,4-oxazin-3(4H)-one, a pharmaceutically acceptable salt thereof.

8. A pharmaceutical composition comprising an effective positive inotropic amount of a compound selected from the group consisting of 7-[4',5'-dihydro-3,-oxo-(2H) pyridazin-6'-yl]-4-methyl-2H-pyrido-[3,2-b]-1,4-oxazin-3(4H)-one, 7-[4',5'-dihydro-2',5'-dimethyl-3,-oxo-(2H) pyridazin-6,-yl]-4-methyl-2H-pyrido[3,2-b]-1,4-oxazin-3 (4H)-one, 7-[4',5'-dihydro-5'-(N,N-dimethylaminomethyl)-3,-oxo-(2H)pyridazin-6'-yl]-4-methyl-2H-pyrido[3,2-b]-1,4-oxazin-3(4H)-one, 7-[4',5'-dihydro-5'-(N-morpholinomethyl)-3-oxo-(2H)pyridazin-6,-yl]-4-methyl-2H-pyrido[3,2-b],-1,4-oxazin-31 (4H)-one, 7-[4',5'-dihydro-5'-(N-morpholinomethyl)-2 -methyl-3,-oxo-(2H) methyl-3'oxo-(2)-pyridazin-6,-yl]-4-methyl-(2H)-pyrido[3,2-b]-1,4-oxazin-3(4H)-one and 7-[3'-oxo-(2H)pyridazin-6,-yl]-2H-pyrido [3,2-b]-1,4-oxazin-3(4H)-one, a pharmaceutically acceptable salt thereof in admixture with a pharmaceutical carrier.

* * * * *